United States Patent
Huang et al.

(10) Patent No.: US 11,377,691 B2
(45) Date of Patent: Jul. 5, 2022

(54) METHODS AND KITS FOR DIAGNOSING KAWASAKI DISEASE AND METHODS FOR TREATING KAWASAKI DISEASE

(71) Applicant: Chang Gung Memorial Hospital, Kaohsiung, Kaohsiung (TW)

(72) Inventors: Ying-Hsien Huang, Kaohsiung (TW); Ho-Chang Kuo, Kaohsiung (TW)

(73) Assignee: Chang Gung Memorial Hospital, Kaohsiung, Kaohsiung (TW)

( * ) Notice: Subject to any disclaimer, the term of this patent is extended or adjusted under 35 U.S.C. 154(b) by 408 days.

(21) Appl. No.: 16/196,092

(22) Filed: Nov. 20, 2018

(65) Prior Publication Data
US 2019/0153081 A1 May 23, 2019

Related U.S. Application Data

(60) Provisional application No. 62/589,345, filed on Nov. 21, 2017.

(51) Int. Cl.
| | |
|---|---|
| C12Q 1/68 | (2018.01) |
| C12Q 1/6883 | (2018.01) |
| C12Q 1/6816 | (2018.01) |
| C12Q 1/6851 | (2018.01) |
| A61P 9/00 | (2006.01) |
| A61K 39/00 | (2006.01) |

(52) U.S. Cl.
CPC ...... *C12Q 1/6883* (2013.01); *A61K 2039/505* (2013.01); *A61P 9/00* (2018.01); *C12Q 1/6816* (2013.01); *C12Q 1/6851* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2013/0129668 A1* 5/2013 Firestein .............. C12Q 1/6883 424/85.1

FOREIGN PATENT DOCUMENTS

EP 2116618 A1 11/2009

OTHER PUBLICATIONS

Kuo et al. Identification of an Association Between Genomic Hypomethylation of FCGR2A and Susceptibility to Kawasaki Disease and Intravenous Immunoglobulin Resistance by DNA Methylation Array. Arthritis & Rheumatology; 2015; vol. 67; No. 3: pp. 828-836. (Year: 2015).*
Kuo et al. Inflammation-Induced Hepcidin is Associated with the Development of Anemia and Coronary Artery Lesions in Kawasaki Disease. J Clin Immunol, 2012 32:746-752. (Year: 2012).*
Karlsson. Evaluation of a competitive hepcidin ELISA assay in the differential diagnosis of iron deficiency anaemia with concurrent inflammation and anaemia of inflammation in elderly patients. Journal of Inflammation; Sep. 2017;14: 21: p. 1-5. (Year: 2017).*
Huang et al. Identifying genetic hypomethylation and upregulation of tolllike receptors in Kawasaki disease. Oncotarget, Jan. 2017, vol. 8, No. 7, p. 11249-11258. (Year: 2017).*
Huang et al. Correlation of HAMP gene polymorphisms and expression with the susceptibility and length of hospital stays in Taiwanese children with Kawasaki disease. Oncotarget; May 2017; vol. 8; No. 31: 51859-51868. (Year: 2017).*
Kuo et al. Arthritis & Rheumatology; 2015; vol. 67; No. 3: 828-836. (Year: 2015).*
Kuo et al. J Clin Immunol; 2012; 32:746-752. (Year: 2012).*
Ho-Chang Kuo et al., "Identification of an association between genomic hypomethylation of FCGR2A and susceptibility to Kawasaki disease and intravenous immunoglobulin resistance by DNA methylation array," Arthritis & Rheumatology, Mar. 2015, pp. 828-836, vol. 67, No. 3.
Ho-Chang Kuo et al., "Inflammation-induced hepcidin is associated with the development of anemia and coronary artery lesions in Kawasaki disease," Journal of Clinical Immunology, Mar. 6, 2012, pp. 746-752, vol. 32.
Search Report for Corresponding Taiwan application No. 107136312, dated Sep. 3, 2019.
Office Action for AU Application No. 2018253505, dated Aug. 4, 2020.
Sung-Chou Li et al., "Major methylation alterations on the CpG markers of inflammatory immune associated genes after IVIG treatment in Kawasaki disease," BMC Medical Genomics, Aug. 2016, vol. 9, (Suppl 1):37, pp. 81-88.
Silvia Udali et al., "DNA methylation and gene expression profiles show novel regulatory pathways in hepatocellular carcinoma," Clin Epigenetics Apr. 2015, 7(1):43.
Natascia Campostrini et al., 'Hepcidin repression by promoter dna hypermethylation in non-viral hepatocellular carcinoma', American Journal of Hematology, Mar. 2016, vol. 91, No. 3, Conference Abstract, Paster #61 (p. E81).
Office Action for JP Application No. 2018-217635 dated Jan. 28, 2020.

(Continued)

*Primary Examiner* — Juliet C Switzer
*Assistant Examiner* — Wahwah T Johnson
(74) *Attorney, Agent, or Firm* — Pilloff Passino & Cosenza LLP; Sean A. Passino; Rachel K. Pilloff

(57) ABSTRACT

The present invention relates to methods that use novel biomarkers for diagnosing and/or treating Kawasaki diseases. The novel biomarkers of the invention show altered cytosine methylations state of certain CpG loci in subject with Kawasaki Disease relative to subject without Kawasaki diseases. Also provided are kits comprising at least one primer or reagent specific for the altered cytosine methylation state of certain CpG loci to detect Kawasaki Disease.

16 Claims, 4 Drawing Sheets
Specification includes a Sequence Listing.

(56) References Cited

OTHER PUBLICATIONS

Ying-Hsien Huang et al., "Correlation of HAMP gene polymorphisms and expression with the susceptibility and length of hospital stays in Taiwanese children with Kawasaki disease," Oncotarget, May 8, 2017, pp. 51859-51868, vol. 8, No. 31.

Ho-Chang Kuo et al., "FCGR2A Promoter methylation and risks for intravenous immunoglobulin treatment responses in kawasaki disease," Mediators Inflamm., Epub May 18, 2015, pp. 1-5, vol. 2015, Article ID 564625.

Ying-Hsien Huang et al., "Identifying genetic hypomethylation and upregulation of toll-like receptors in Kawasaki disease," Oncotarget, Feb. 14, 2017, pp. 11249-11258, vol. 8, No. 7.

* cited by examiner

SEQUENCE LISTING

<160> NUMBER OF SEQ ID NOS: 9

<210> SEQ ID NO 1
<211> LENGTH: 122
<212> TYPE: DNA
<213> ORGANISM: Homo sapiens

<400> SEQUENCE: 1

```
tctgccggct gagggtgaca caaccctgtt ccctgtcgct ctgttcccgc ttatctctcc    60
cgccttttcg gcgccaccac cttcttggaa atgagacaga gcaaagggga gggggctcag   120
ac                                                                  122
```

<210> SEQ ID NO 2
<211> LENGTH: 122
<212> TYPE: DNA
<213> ORGANISM: Homo sapiens

<400> SEQUENCE: 2

```
agggtgacac aaccctgttc cctgtcgctc tgttcccgct tatctctccc gccttttcgg    60
```

-continued cgccaccacc ttcttggaaa tgagacagag caaaggggag ggggctcaga ccaccgcctc    120
cc                                                                  122

<210> SEQ ID NO 3
<211> LENGTH: 122
<212> TYPE: DNA
<213> ORGANISM: Homo sapiens

<400> SEQUENCE: 3
gtcactcggt cccagacacc agagcaagct caagacccag cagtgggaca gccagacaga    60
cggcacgatg gcactgagct cccagatctg ggccgcttgc ctcctgctcc tcctcctcct    120
cg                                                                  122

<210> SEQ ID NO 4
<211> LENGTH: 122
<212> TYPE: DNA
<213> ORGANISM: Homo sapiens

<400> SEQUENCE: 4
gctggcgagg aggaggagga gcaggaggca agcggcccag atctgggagc tcagtgccat    60
cgtgccgtct gtctggctgt cccactgctg ggtcttgagc ttgctctggt gtctgggacc    120
ga                                                                  122

<210> SEQ ID NO 5
<211> LENGTH: 122
<212> TYPE: DNA
<213> ORGANISM: Homo sapiens

<400> SEQUENCE: 5
acctcaagtg ggctgcctgc ctcaacctcc caaagtgctg ggattacagg catgagccac    60
cgtgcctgtc ctggttcctg ttcagctgcc agtactcctg agacgtcctg agctctgctc    120
ag                                                                  122

<210> SEQ ID NO 6
<211> LENGTH: 122
<212> TYPE: DNA
<213> ORGANISM: Homo sapiens

<400> SEQUENCE: 6
gatccctcct ttactctggg gggcgagggg accaggagcc ttagggcagg caccgcccac    60
cggcctccac cccagggatg actcccgagc cccatggctg ttggactttc tgcatgcaag    120
gg                                                                  122

<210> SEQ ID NO 7
<211> LENGTH: 122
<212> TYPE: DNA
<213> ORGANISM: Homo sapiens

<400> SEQUENCE: 7
gaggccggcg tggcggcgg cggctgcgtg gtggtggcgg gcgtcactgc cgggtgccct     60 cgccaccat ctccaggttg tgctgctgca gctgggctcg aagcagggcg ttctcattct    120
tc                                                                  122

<210> SEQ ID NO 8
<211> LENGTH: 122
<212> TYPE: DNA
<213> ORGANISM: Homo sapiens

```
<400> SEQUENCE: 8
aacacagcag  ggcacagcgg  tatgctagac  ctggctcaac  atagcagacc  atgcacatct      60
cgaaactctg  cattcagtgg  catcatgctg  gtatcctgaa  atcagcagca  gtgggagtct     120
tg                                                                         122

<210> SEQ ID NO 9
<211> LENGTH: 122
<212> TYPE: DNA
<213> ORGANISM: Homo sapiens

<400> SEQUENCE: 9
acagggaaca  gggttgtgtc  accctcagcc  ggcagaggtg  tgttcagggg  gtggggcaga      60
cggggtcaca  gacacacact  gctcaccagc  catctgggga  gcccttcccc  catcacgatg     120
tc                                                                         122
```

METHODS AND KITS FOR DIAGNOSING KAWASAKI DISEASE AND METHODS FOR TREATING KAWASAKI DISEASE

CROSS-REFERENCE TO RELATED APPLICATIONS

This application claims the benefit of U.S. Patent Application No. 62/589,345, filed on Nov. 21, 2017, the disclosure of which is incorporated by reference herein in its entirety.

BACKGROUND OF THE INVENTION

Kawasaki disease (KD), also referred to as mucocutaneous lymph node syndrome of unknown etiology, is an acute childhood vasculitis syndrome that affects the walls of both small- and medium-sized blood vessels (vasculitis), especially coronary arteries. The incidence of KD was more than 10 times higher in Asian children compared to that of American and European children.

The earliest and most obvious symptom of KD is fever for at least five days. If left untreated, it leads to severe coronary artery complications, including coronary artery dilation, fistula formations, coronary artery aneurysms (CAAs) and myocardial infarction. The successful detection of KD within the first 10 days of fever onset followed by high dose intravenous immunoglobulin (IVIG) can greatly reduce the incidence of coronary artery aneurysms from 20%-25% to 3-5%.

There is currently no definitive laboratory diagnostic test for KD and the diagnosis of KD is largely a clinical one, based on the American Heart Association (AHA) 2004 diagnostic criteria. These diagnosis criteria include fever over 5 days, bilateral nonsuppurative conjunctivitis, changes to the mucous membranes, indurative angioedema of the hands and feet, dysmorphous skin rashes and acute nonpurulent cervical lymphadenopathy >1.5 cm in diameter.

However, the AHA diagnostic criteria for KD differ slightly from Japan Circulation Society guideline for KD, which makes the clinical diagnosis of KD perplexing. In addition, infectious diseases, such as staphylococcal or streptococcal infection, may mimic KD. It can be difficult for the clinicians to accurately diagnose KD and promptly administer IVIG to prevent coronary artery disease in the affected children.

There is an unmet need for an economical and accurate laboratory diagnostic test for KD and the present invention satisfy this and other needs.

BRIEF SUMMARY OF THE INVENTION

In one embodiment, the present invention discloses methods for detecting Kawasaki disease in a subject, comprising the step of (a) obtaining a sample from the subject; (b) determining the cytosine methylation state of at least two CpG dinucleotide selected from SEQ ID NO:1, SEQ ID NO:2, SEQ ID NO: 3, SEQ ID NO:4, or SEQ ID NO:5 from the sample of the subject; and (b) identify the subject as having KD if the subject has cytosine hypomethylation of at least one CpG dinucleotide in step (a) as compared to a control sample.

In another embodiment, the present invention discloses methods for detecting Kawasaki disease in a subject, comprising the step of (a) determining the cytosine methylation state of a CpG dinucleotide selected from SEQ ID NO:1, SEQ ID NO:2 or the combination thereof, and (b) measuring the expression level of hepcidin.

In another embodiment, the present invention provides method for treating a subject with KD, comprising the step of identifying the subject with KD by the methods disclosed herein, and administering a therapeutic agent for KD.

The present invention also discloses kits for detecting Kawasaki disease in a subject, comprising at least one primer or reagent specific for determining the cytosine methylation state of at least one CpG dinucleotides selected from SEQ ID NO:1, SEQ ID NO:2, SEQ ID NO: 3, SEQ ID NO:4, or SEQ ID NO:5.

Also provided are kits for detecting Kawasaki disease in a subject, comprising (a) at least one primer or reagent specific for determining the cytosine methylation state of the following CpG dinucleotides: SEQ ID NO:1, SEQ ID NO:2 or the combination thereof; and (b) an agent for measuring the expression level of hepcidin.

The use of the kit described herein for detecting Kawasaki disease is also provided.

The present invention provides primer or reagent for determining the cytosine methylation state of at least one CpG dinucleotide selected from SEQ ID NO:1, SEQ ID NO:2, SEQ ID NO: 3, SEQ ID NO:4, SEQ ID NO:5 in the manufacture of a kit for detecting KD in a subject.

Further provided is a method for reducing coronary artery disease in a subject suspected of having Kawasaki disease, comprising: (a) obtaining a sample from the subject; (b) determining the cytosine methylation state of at least one CpG dinucleotide selected from SEQ ID NO:1, SEQ ID NO:2, SEQ ID NO: 3, SEQ ID NO:4, or SEQ ID NO:5 from the sample of the subject; (c) identifying the subject as having KD if the cytosine methylation of at least one CpG dinucleotide in step (b) is lower compared to a control or KD-free sample; and (d) administering the subject a therapeutic agent for KD. In one embodiment, the method further comprises measuring the expression level of hepcidin. In another embodiment, the therapeutic agent is intravenous immunoglobulin (IVIG). In another embodiment, the therapeutic agent increases the cysteine methylation of at least one CpG dinucleotide selected from SEQ ID NO:1, SEQ ID NO:2, SEQ ID NO: 3, SEQ ID NO:4, or SEQ ID NO:5 in the subject.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

Illustrative embodiments of the present invention are described in detail below with reference to the following Figures.

DETAILED DESCRIPTION OF THE INVENTION

Figure 1:
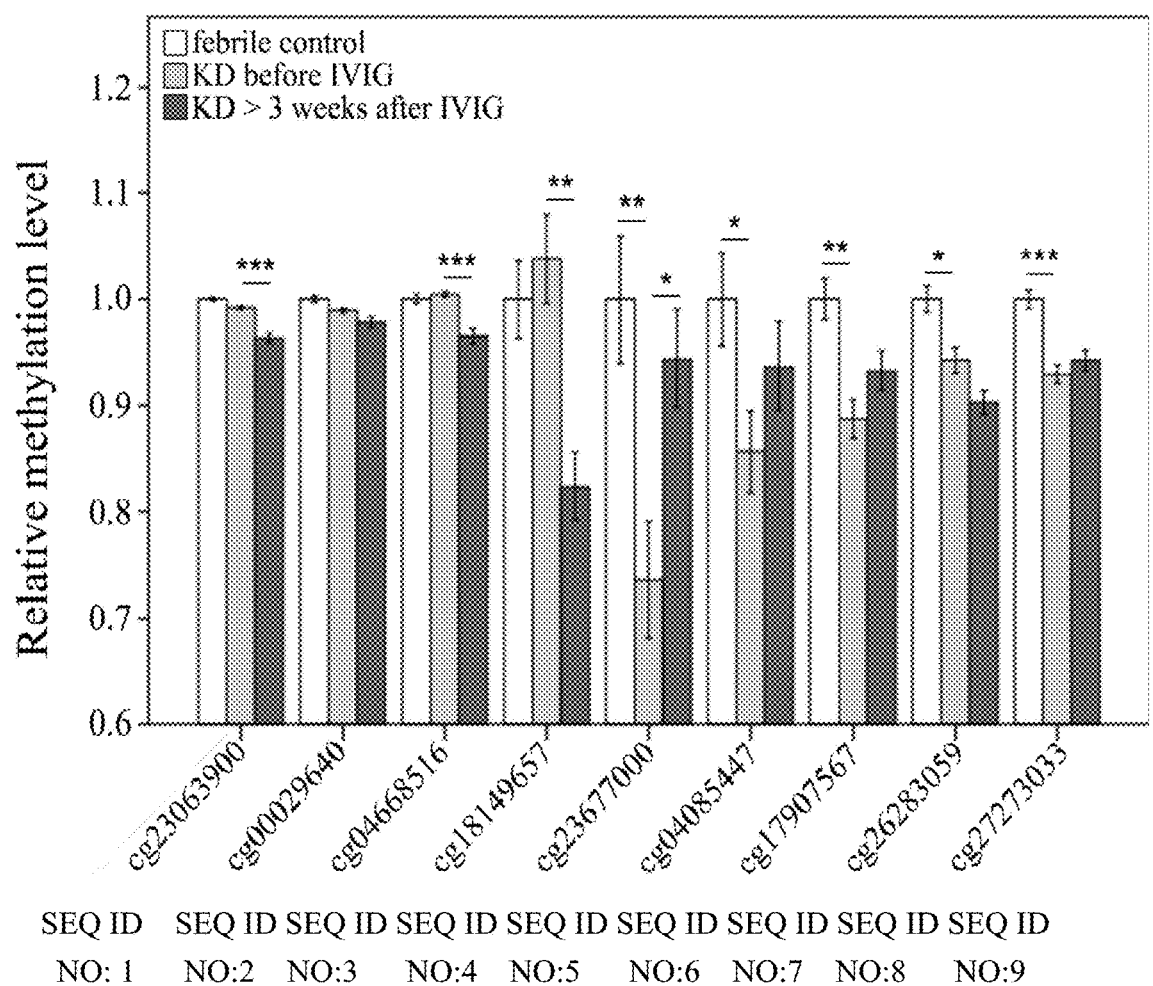
FIG. 1 is a bar graph illustrating the relative methylation level of the following CpG dinucleotides: cg23677000 (SEQ ID NO:1), cg04085447 (SEQ ID NO:2), cg17907567 (SEQ ID NO:3), cg 26283059 (SEQ ID NO:4), (cg27273033 SEQ ID NO:5), cg23063900 (SEQ ID NO:6), cg00029640 (SEQ ID NO:7), cg 04668516 (SEQ ID NO:8), cg18149657 (SEQ ID NO:9) in 18 febrile control samples, 18 KD samples before IVIG treatment and 18 KD samples after IVIG treatment, using Infinium HumanMethylation450 BeadChip (Illumina, USA). "*", "" and "*" denote p<0.001, p<0.01 and p<0.05, respectively.

As used herein, the articles "a" and "an" refer to one or more than one (i.e., at least one) of the grammatical object of the article.

The term "subject" may refer to a vertebrate suspected of having KD. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.).

As used herein, "sample" refers to a composition containing a material to be detected, and includes e.g. "biological samples", which refer to any material obtained from a living source, for example an animal such as a human or other mammal that can suffer from KD. The biological sample can be in any form, including a solid material such as a tissue, cells, a cell pellet, a cell extract, a surgical sample, a biopsy or fine needle aspirate, or it can be in the form of a biological fluid such as urine, whole blood, plasma, or serum, or any other fluid sample produced by the subject such as saliva.

The term "methylation level" as applied to a gene refers to whether one or more cytosine residues present in a CpG context have or do not have a methylation group. Methylation level may also refer to the fraction of cells in a sample that do or do not have a methylation group at positions C5 or N4 of cytosine. The methylation of the CpG dinucleotide can reside in non-coding transcriptional control sequences (e.g. promoters, enhancers, etc.) or in coding sequences, including introns and exons of the associated genes.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The term CpG locus is also known as CpG dinucleotide or CpG site.

All numbers herein may be understood as modified by "about." As used herein, the term "about," is meant to encompass variations of ±15% from the specified value.

Methods for Diagnosing Kawasaki Disease

The present invention is based, in part, on the identification of differential methylation level of specific CpG dinucleotides is predictive of Kawasaki disease. Some embodiments of the present invention are directed to methods of diagnosing whether a subject has, or is at risk for developing KD, comprising the steps of a) contacting genomic DNA from a sample of the subject with at least one reagent, or series of reagents that distinguishes between methylated and non-methylated CpG dinucleotide(s) listed in Table 1, and b) identifying the subject has or is at risk of developing KD if the subject level has a lower methylation level of at least one CpG dinucleotide or locus listed in Table 1 relative to that of the KD-free or control sample.

In another embodiment, the methods comprise obtaining a biological sample from an individual; and determining the methylation level of at least one cytosine within a DNA region in a sample from an individual where the DNA region is at least 90%, 91%, 92%, 93%, 94%, 95%, 96%, 97%, 98%, or 99% identical to, or comprises, a sequence selected from the group consisting of SEQ ID NOS.: 1-5.

TABLE 1 shows the chromosomal position, the SEQ ID NO and the DNA sequence

| CpG locus* | Chromosome/ Coordinate | SEQ ID NO | Sequence |
|---|---|---|---|
| cg23677000 | 19/35,773,317 | 1 | tctgccggctgagggtgacacaaccctgttccctgtcgctct gttcccgcttatctctcc[cg]cctttcggcgccaccaccttct tggaaatgagacagagcaaaggggaggggctcagac |
| cg04085447 | 19/35773328 | 2 | agggtgacacaaccctgttccctgtcgctctgttcccgcttat ctctcccgccttttcgg[cg]ccaccaccttcttggaaatgag acagagcaaaggggaggggctcagaccaccgcctccc |

TABLE 1-continued shows the chromosomal position, the SEQ ID NO and the DNA sequence

| CpG locus* | Chromosome/ Coordinate | SEQ ID NO | Sequence |
|---|---|---|---|
| cg17907567 | 19/35773474 | 3 | gtcactcggtcccagacaccagagcaagctcaagaCcca gcagtgggacagccagacaga[cg]gcacgatggcactg agctcccagatctgggccgcttgcctcctgctcctcctcc tcg |
| cg26283059 | 19/35773480 | 4 | gctggcgaggaggaggaggagcaggaggcaagcggcc cagatctgggagctcagtgccat[cg]tgccgtctgtctggct gtcccactgctgggtcttgagcttgctctggtgtctgggaccg a |
| cg27273033 | 19/35773719 | 5 | acctcaagtgggctgcctgcctcaacctcccaaagtgctgg gattacaggcatgagccac[cg] tgcctgtcctggttcctgttcagctgccagtactcctgagacg tcctgagctctgctcag |

*The "CpG loci" column is the reference number provided by Illumina's ® Golden Gate and Infinium ® Assays for methylation.

In one embodiment, a decreased in the methylation level at least one of the following CpG loci (may be determined by any method set forth herein or known to those of skill in the art) is indicative the subject has KD or may be at a risk of developing KD: cg23677000, cg04085447, cg17907567, cg26283059, or cg27273033. In another embodiment, the methylation level of at least two of the forgoing CpG loci may be determined (by any method set forth herein) to identify whether a subject has or may be at a risk of developing KD. In certain embodiments, the level of hepcidin is measured. In some embodiments, the methylation level of two or more CpG dinucleotides and/or the measurement of hepcidin level offer a higher accuracy, sensitivity or specificity for KD diagnosis.

In some embodiments, the methylation level of the chromosomal DNA within a DNA region or portion thereof (e.g., at least one cytosine residue) selected from the CpG loci identified in Table 1 is determined. In some embodiments, the methylation level of all cytosines within at least 20, 50, 100, 200, 500 or more contiguous base pairs of the CpG loci is also determined. For example, in one embodiment, the methylation level of the cytosine at cg23677000 is determined.

In some embodiments of the invention, the methylation level of a control or KD-free CpG loci is predetermined and then normalized. Typically the control locus will have a known, relatively constant, methylation level. The predetermined methylation level in a KD-free or control sample is from a representative pool of KD-free individuals, and are a mean, median or other statistically manipulated or otherwise summarized or aggregated representative of methylation level in the KD-free or control samples.

A lower methylation level or hypomethylation is a relative term and can be determined by comparison of the methylation level of the CpG loci in Table 1 in the test KD sample to that from the referenced control level. In some embodiments, methylation level of the CpG loci in Table 1 in a test sample is 1%, 5%, 10%, 15%, 20%, 25%, 30%, 35%, 40%, 45%, 50%, 55%, 60%, 65%, 70%, 75%, 80%, 85%, 90%, 95% or 100% lower than that of a KD-free or control subjects.

Any method for detecting methylation levels of an DNA can be used in the methods of the present invention. Non limiting examples of methylation level detection method include methylation sensitive restriction enzyme analysis, chemical analysis by means of treatment with a reagent comprising bisulfite, disulfite, hydrogen sulfite or combinations thereof, or pyrosequencing.

When sodium bisulfite is contacted to DNA, unmethylated cytosine is converted to uracil, while methylated cytosine is not modified. Such additional embodiments include the use of array-based assays such as the Illumina® Human Methylation450 BeadChip and multiplex PCR assays.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602.

Additional methylation level detection methods include, but are not limited to, nucleic acid amplification, polymerase chain reaction (PCR), methylation specific PCR (MCP), methylated-CpG island recovery assay (MIRA), combined bisulfite-restriction analysis (COBRA), single-strand conformation polymorphism (SSCP) analysis, restriction analysis and microarray analysis (Lian Z Q et al, screening of significantly hypermethylated genes in breast cancer using microarray-based methylated-CpG island recovery assay and identification of their expression levels, International Journal of Oncology, 41: 629-638, 2012).

In an embodiment, the method further comprises measuring the plasma hepcidin level. Measuring plasma hepcidin level can be achieved using any method known in the art or described herein, such as enzyme-linked immunoassay (ELISA). In another embodiment, the method further comprises measuring the hepcicin miRNA expression. Measuring the level of hepcidin miRNA expression refers to quantifying the amount of miRNA present in a sample and can be achieved using any method known in the art or described herein, such as by real-time PCR, Northern blot analysis, or other techniques well known to those of skill in the art. Measuring the expression level of hepcidin miRNA includes measuring the expression of either a mature form of miRNA or a precursor form that is correlated with miRNA expression.

In a particular embodiment, the level of at least one miRNA is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA reagents complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

In some embodiments, quantitative RT-PCR is used to measure the miRNA of hepcidin. Quantitative RT-PCR (qRT-PCR) is a modification of polymerase chain reaction used to rapidly measure the quantity of a product of polymerase chain reaction. There are several variations of the qRT-PCR method known in the art, include, but are not limited to, via agarose gel electrophoresis, the use of SYBR Green (a double stranded DNA dye), and the use of a fluorescent reporter reagent.

The determination of differential methylation level of at least one CpG loci listed in Table 1 in KD and non-KD subject, allows the use of this information in a number of ways. For example, a subject can be promptly treated with a therapeutic agent for KD (for example, one or more doses of IVIG, aspirin, anti-TNF-α agent, corticosteroid, cyclosporin, IL-1 inhibitors (anakinra and canakinumab), cyclophosphamide, Rituximab, Tocilizumab, Pentoxifylline, plasmapheresis or combination thereof)) once the diagnosis of KD is confirmed with the methods disclosed herein. In an exemplary embodiment, therapeutic agent increases the cysteine methylation of at least one CpG dinucleotide selected from SEQ ID NO:1, SEQ ID NO:2, SEQ ID NO: 3, SEQ ID NO:4, or SEQ ID NO:5 in the subject by at least 1%, 5%, 10%, 20%, 30%, 40%, 50%, 60%, 70%, 80%, 90% or 100%. In another embodiment, the administration of the therapeutic agent occurs within about 10 days from first onset of fever in the subject. In another example, a particular treatment regime may be evaluated (e.g., to determine whether a therapy is effective to prevent the coronary artery complications in a subject with KD). Similarly, diagnosis may be done or confirmed by comparing the methylation level of at least one CpG loci listed in Table 1 in a test sample with known expression profiles from non-KD samples. Furthermore, these methylation profiles allow screening of drug candidates that enhances methylation expression in KD or convert a poor prognosis profile to a better prognosis profile.

Kits for Diagnosing Kawasaki Disease

The present invention also provides kits for use in diagnosing KD. The kit comprises at least one primer or reagent specific for determining the cytosine methylation state of at least one CpG dinucleotides selected from SEQ ID NO:1, SEQ ID NO:2, SEQ ID NO: 3, SEQ ID NO:4, or SEQ ID NO:5.

In one embodiment, kits for detection of methylation level can comprise at least one primer that hybridizes to one of the CpG loci identified in Table 1 (or a nucleic acid sequence at least 90% identical to the CpG loci of Tale 1), or that hybridizes to a region of DNA flanking one of the CpG identified in Table 1, at least one reagent for detection of methylation selected from sodium bisulfite, a methylation-sensitive or methylation-dependent restriction enzyme, or amplification (e.g., PCR) reagents. The kits can provide solid supports in the form of an assay apparatus that is adapted to use in the assay. The kits may further comprise detectable labels or instruction for KD diagnosis. Other materials useful in the performance of the assays can also be included in the kits, including test tubes, transfer pipettes, and the like.

In some embodiments, use of a microarray is desirable. A microarray is a microscopic, ordered array of nucleic acids, proteins, small molecules, cells or other substances that enables parallel analysis of complex biochemical samples. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

In one embodiment, the microarray comprises specific primer oligonucleotides for determining the methylation states of at least one CpG loci in Table 1.

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Description of Materials and Methods Used in the Examples

Patients

A total of 259 subjects from Kaohsiung Chang Gung Memorial Children's Hospital in Taiwan were enrolled in this study. Of those, 18 subjects were fever controls (with fever but not KD), and the remaining 18 subjects were KD patients who had blood samples collected prior to and 3 weeks after IVIG treatment. The patients in the fever control were diagnosed with upper respiratory tract infection or urinary tract infection.

Experiment Design

The collected whole blood samples were subjected to white blood cell (WBC) enrichment, followed by DNA isolation. The DN samples were treated with bisulfite as described in Huang Y H et al. (*Oncotarget* 2017, 8(7):11249-11258).

DNA Methylation Profiling with Illumina M450K Bead-Chip

Illumina HumanMethylation450 (M450K) BeadChip (Illumina, USA) was used to carry out genome-wide screening of DNA methylation patterns. 200 ng of bisulfite-converted genomic DNA was applied to each M450K BeadChip assay, according to the manufacturer's instructions. Methylation percentage of cytosine ((3 value) was calculated for each CpG dinucleotide in each sample.

Measurement of Hepcidin by Enzyme-Linked Immunoassay (ELISA)

The plasma hepcidin level was measured using an ELISA kit (commercially available from Bachem Bioscience, UK).

Validation of DNA Methylation Array by Pyrosequencing Assay.

Genomic DNA (0.5 µg) was bisulfite modified using an EZ DNA methylation kit (Zymo Research, USA) and eluted in 20 µl of Tris buffer (10 mM). Polymerase chain reaction (PCR) was carried out in a 25-µl reaction mixture containing 25 ng of bisulfite-converted DNA, 1× PyroMark PCR Master Mix (Qiagen, Germany), and 0.2 µM HAMP biotinylated forward primer ATTTTTGTAGGTTGAGGGTGA-TATAATT (SEQ ID NO: 10), with the biotinylated reverse primer CCTCCCCTTTACTCTATCTCAT (SEQ ID NO:

11). The following PCR parameters were used: 95° C. for 5 minutes, then 45 cycles of 95° C. for 30 seconds, followed by 52° C. for 30 seconds, and 72° C. for 30 seconds, with a final extension at 72° C. for 5 minutes. Following amplification, the biotinylated PCR products were purified and incubated with the sequencing primer TTTGTTTTAGTTT-ATTTT (SEQ ID NO: 12), which was designed to bind adjacent to the CpG sites of interest. Pyrosequencing was conducted using a PyroMark Q24 instrument (Qiagen) with subsequent quantification of methylation levels determined with PyroMark Q24 1.010 software.

Statistical Analysis

All data are presented as mean±standard error. Student's t-test or one-way ANOVA, were used to analyze quantitative data. Data before and after IVIG treatment were analyzed using the paired sample t-test. All statistical analyses were carried out using SPSS version 22.0 for Windows XP (SPSS, Inc., Chicago, USA), and a two-sided p-value less than 0.05 was considered statistically significant.

Results

FIG. 1 shows statistically significant hypomethylation of the following CpG dinucleotides between KD patients and febrile control: cg23677000, cg04085447, cg17907567, cg 26283059, and cg27273033.

Figure 2:
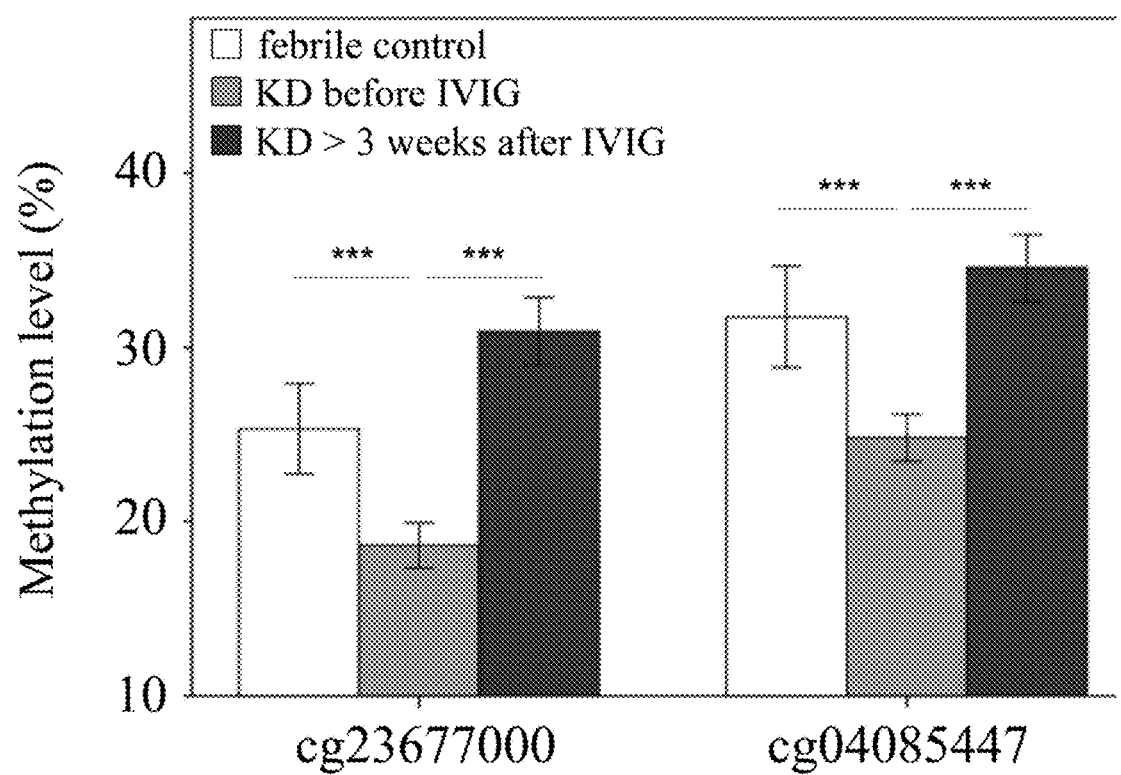
FIG. 2 is a bar graph illustrating the CpG dinucleotide methylation level at cg23677000 and cg04085447 in 113 febrile control samples, 92 KD samples before IVIG treatment and 16 KD samples after IVIG treatment, using target specific Infinium HumanMethylation450 BeadChip. "***", denotes p<0.001.

To ensure that this hypomethylation of CpG dinucleotides is robust enough at distinguishing KD from non-KD patients, the above methylation results were validated in a separate patient cohort with 92 KD patients before and 16 KD patients after IVIG treatment and 113 febrile controls, using a target-specific sequencing of the top 2 CpG dinucleotides: cg23677000 and cg04085447 via pyrosequencing. FIG. 2 shows the validated methylation status of cg23677000 and cg04085447, which shows statistically significant hypomethylation of cg23677000 and cg04085447 in KD patients before IVIG treatment compared to the febrile control. (P<0.001 and <0.001, respectively). FIG. 2 further illustrates the methylation status of cg23677000 and cg04085447 in KD patients significantly increased after IVIG treatment. (P<0.001 and <0.001, respectively). The results of methylation analysis were consistent between methylation array and pyrosequencing.

Figure 3:
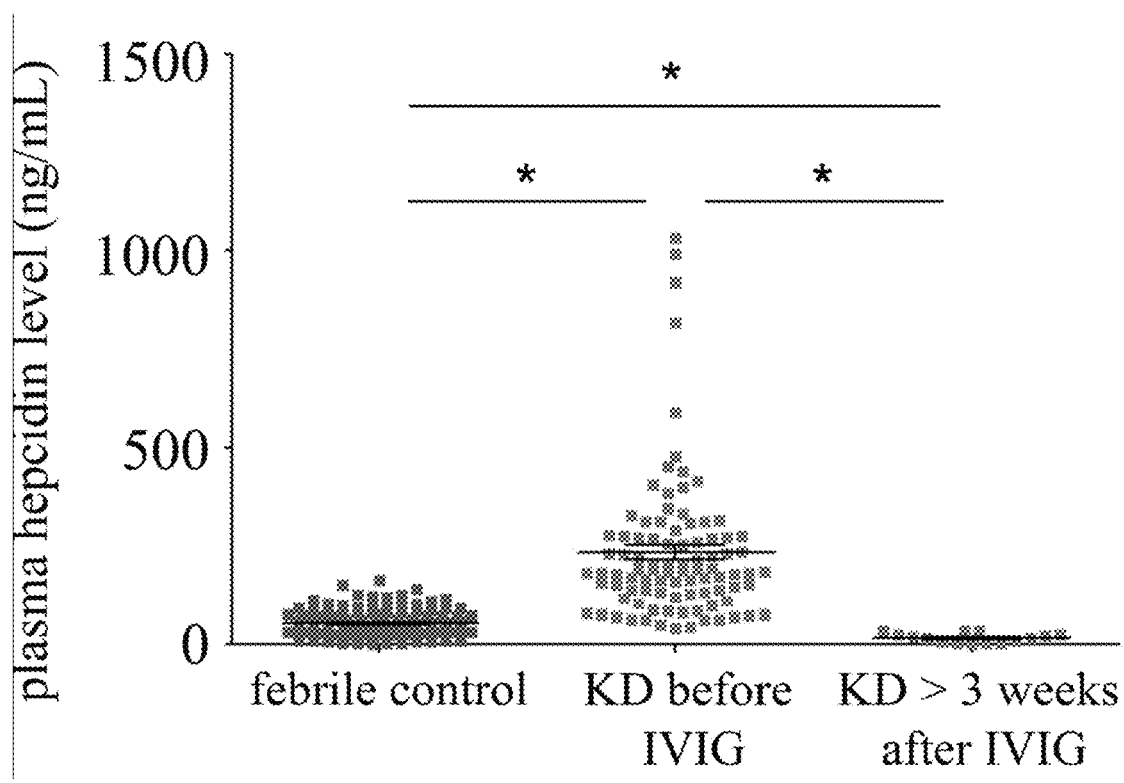
FIG. 3 illustrates plasma hepcidin levels in non-KD febrile controls (n=113) and 92 KD samples before IVIG treatment and 16 KD samples after IVIG treatment using the Bio-Plex system by ELISA. Each dot represents a single individual. "*" denotes P<0.05 using unpaired Student t test.

Plasma hepcidin levels were measured in non-KD febrile controls (n=113) and KT patients before (N=92) and after (N=16) IVIG treatment using the Bio-Plex system by ELISA. FIG. 3 shows plasma hepcidin level is significantly higher in KD patients compared to febrile control.

Figure 4A:
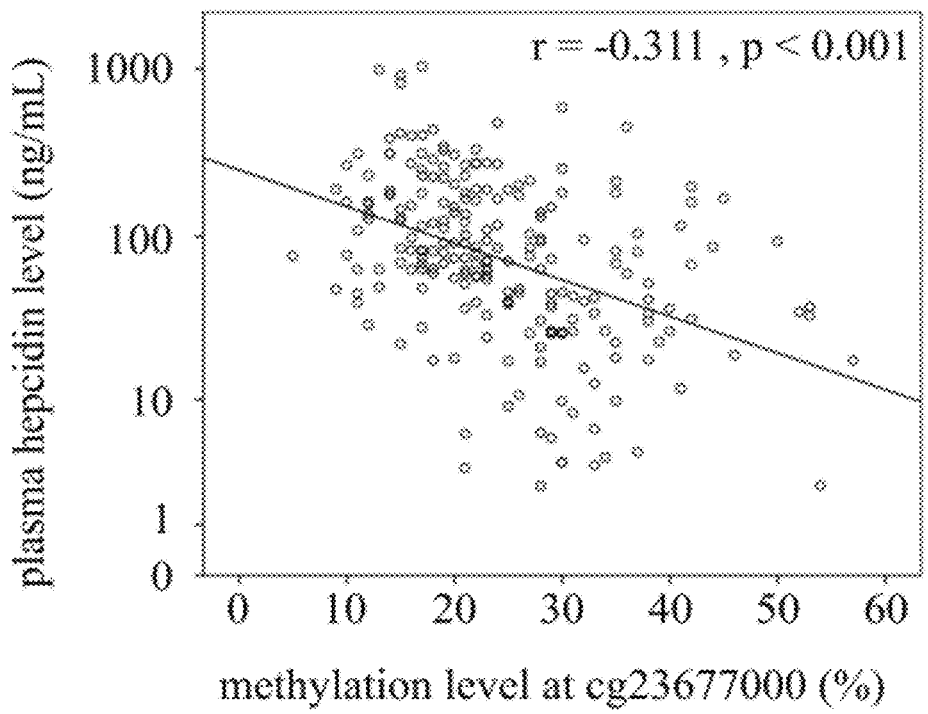
FIG. 4A and FIG. 4B are scatter plots of plasma hepcidin levels and CpG dinucleotide methylation level at cg23677000 and cg04085447 respectively to demonstrate plasma hepcidin level was negatively correlated with DNA methylation level (Pearson's correlation coefficient (N=209 and p<0.001, respectively).
Figure 4B:
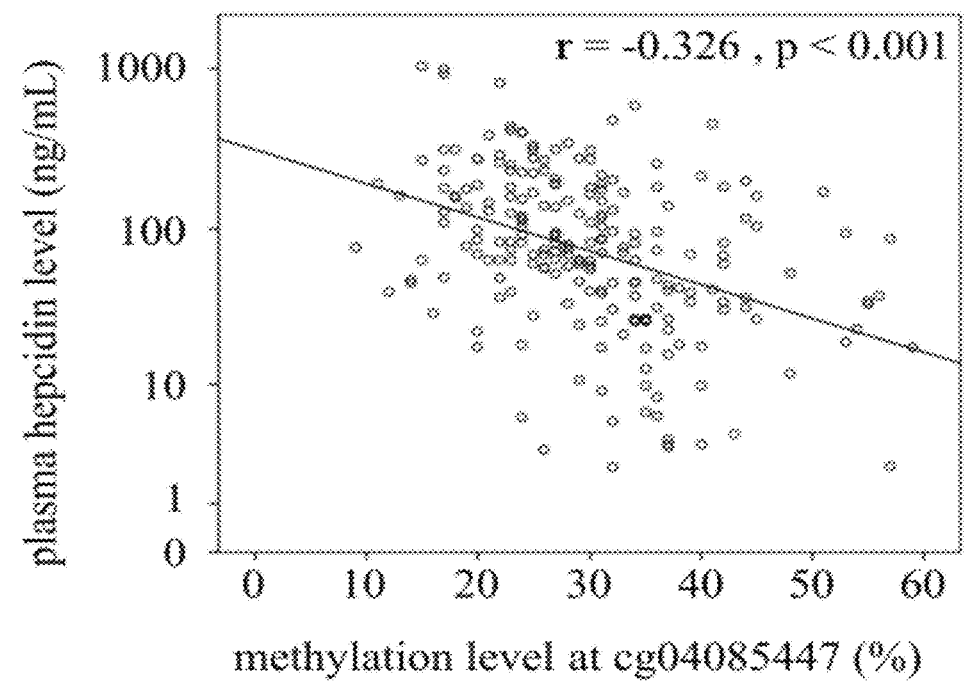

FIG. 4A and FIG. 4B shows the negative correlation of plasma hepcidin levels and methylation status of cg23677000 and cg04085447 (R=−0.311, p<0.001, and R=−0.326, p<0.001, respectively).

Support Vector Machines (SVM) Classification Model

SVM classification model in Kuo H C et al. (*The Journal of allergy and clinical immunology* 2016, 138(4):1227-1230) was developed to discriminate febrile control from KD subjects. The methylation percentages of cg23677000 and cg04085447 and the plasma ELISA level of hepcidin were SVM vectors for the SVM classification model. The model included 66 KD subjects and 74 febrile control subjects as the training set and 26 KD subjects and 39 febrile control subjects as the blind test set. The three SVM vectors of the training set were used to train the SVM model based on 5-fold cross validation policy. Given the specified parameters (cost=2 and gamma=1). The KD-specific SVM alignment model derived from above was used to calculate the sensitivity, specific and accuracy of the three SVM vectors and the results are shown in Table 2.

TABLE 2

The sensitivity, specificity and accuracy of the methylation percentages of cg23677000 and cg04085447, and the plasma ELISA level of hepcidin in KD diagnosis.

| KD biomarker | Sensitivity | Specificity | Accuracy | P value |
|---|---|---|---|---|
| cg23677000 | 76.25% | 55.40% | 0.69 | 0.00015 |
| cg04085447 | 65.00% | 82.43% | 0.78 | 0.00046 |
| hepcidin | 77.5% | 81.08% | 0.88 | $6.78 \times 10^{-13}$ |
| cg23677000 + cg04085447 | 88.75% | 95.95% | 0.96 | |
| cg23677000 + hepcidin | 96.25% | 98.65% | 0.99 | |
| cg04085447 + hepcidin | 93.75 | 94.59% | 0.98 | |
| cg23677000 + cg04085447 + hepcidin | 100% | 100% | 1 | |

What is claimed is:

1. A method for treating Kawasaki disease (KD) in a subject in need thereof, comprising the steps of:
   (a) obtaining a sample from the subject, wherein the subject exhibits one or more symptoms of KD or is at risk of developing KD;
   (b) measuring the cytosine methylation state of at least one CpG dinucleotide selected from cg23677000, cg04085447, cg17907567, cg26283059 or cg27273033 from the sample of the subject;
   (c) identifying the subject as having KD or at risk of developing KD by identifying that at least one CpG dinucleotide measured in step (b) is lower compared to the corresponding CpG in a control or a KD-free sample; and
   (d) administering a therapeutic agent for KD to the subject having KD or at risk of developing KD.

2. The method of claim 1, wherein the CpG dinucleotides are cg23677000 and cg04085447.

3. The method of claim 1, further comprising measuring the expression level of hepcidin.

4. The method of claim 1, wherein the sample is selected from the group consisting of biopsy, blood, plasma, serum, lymphatic fluid, lymphatic tissue, cerebrospinal fluid, bone marrow, saliva and combinations thereof.

5. The method of claim 1, wherein measuring the cytosine methylation state comprises use of one or more methods selected from the group consisting of nucleic acid amplification, polymerase chain reaction (PCR), methylation specific PCR (MCP), methylated-CpG island recovery assay (MIRA), combined bisulfite-restriction analysis (COBRA), pyrosequencing, single-strand conformation polymorphism (SSCP) analysis, restriction analysis and microarray analysis.

6. The method of claim 3, wherein the expression level of hepcidin is measured by an ELISA or real-time PCR.

7. The method of claim 1, wherein the therapeutic agent is intravenous immunoglobulin (IVIG), aspirin, anti-TNF-α agent, corticosteroid, cyclosporin, IL-1 inhibitor, cyclophosphamide, rituximab, tocilizumab, pentoxifylline, plasmapheresis, or a combination thereof.

8. The method of claim 1, wherein the therapeutic agent is anakinra, canakinumab, or a combination thereof.

9. A method for reducing coronary artery disease in a subject suspected of having Kawasaki disease (KD), comprising:
   (a) obtaining a sample from the subject, wherein the subject exhibits one or more symptoms of KD or is at risk of developing KD;
   (b) measuring the cytosine methylation state of at least one CpG dinucleotide selected from cg23677000, cg04085447, cg17907567, cg26283059 or cg27273033 from the sample of the subject;
   (c) identifying the subject as having KD or at risk of developing KD by identifying that at least one CpG dinucleotide measured in step (b) is lower compared to the corresponding CpG in a control or a KD-free sample; and
   (d) administering a therapeutic agent for KD to the subject having KD or at risk of developing KD.

10. The method of claim 9, wherein the therapeutic agent is intravenous immunoglobulin (IVIG).

11. The method of claim 9, further comprising measuring the expression level of hepcidin.

12. The method of claim 9, wherein the sample is selected from the group consisting of biopsy, blood, plasma, serum, lymphatic fluid, lymphatic tissue, cerebrospinal fluid, bone marrow, saliva and combinations thereof.

13. The method of claim 9, wherein measuring the cytosine methylation state comprises use of one or more methods selected from the group consisting of nucleic acid amplification, polymerase chain reaction (PCR), methylation specific PCR (MCP), methylated-CpG island recovery assay (MIRA), combined bisulfite-restriction analysis (COBRA), pyrosequencing, single-strand conformation polymorphism (SSCP) analysis, restriction analysis and microarray analysis.

14. The method of claim 11, wherein the expression level of hepcidin is measured by an ELISA or real-time PCR.

15. The method of claim 9, wherein the therapeutic agent is intravenous immunoglobulin (IVIG), aspirin, anti-TNF-α agent, corticosteroid, cyclosporin, IL-1 inhibitor, cyclophosphamide, rituximab, tocilizumab, pentoxifylline, plasmapheresis, or a combination thereof.

16. The method of claim 9, wherein the therapeutic agent is anakinra, canakinumab, or a combination thereof.

* * * * *